US005843886A

United States Patent [19]
Weiner et al.

[11] Patent Number: 5,843,886
[45] Date of Patent: *Dec. 1, 1998

[54] METHOD OF TREATING OR PREVENTING TYPE 1 DIABETES BY ORAL ADMINISTRATION OF INSULIN

[75] Inventors: Howard L. Weiner, Brookline; George Eisenbarth, Wellesley; David Allen Hafler, West Newton; Zhengi Zhang, Walden, all of Mass.

[73] Assignee: Autoimmune, Inc., Lexington, Mass.

[*] Notice: The term of this patent shall not extend beyond the expiration date of Pat. Nos. 5,763,396 and 5,643,868.

[21] Appl. No.: 461,588

[22] Filed: Jun. 2, 1995

Related U.S. Application Data

[63] Continuation of Ser. No. 235,121, Apr. 28, 1994, abandoned, which is a continuation of Ser. No. 70,020, May 28, 1993, abandoned, which is a continuation of Ser. No. 896,484, Jun. 2, 1992, abandoned, which is a continuation of Ser. No. 595,468, Oct. 10, 1990, abandoned.

[51] Int. Cl.$^6$ .................................................. A61K 38/28
[52] U.S. Cl. ................................................ 514/3; 424/434
[58] Field of Search ................................ 514/3; 424/434

[56] References Cited

U.S. PATENT DOCUMENTS

| 3,561,444 | 2/1971 | Boucher ................................... 128/194 |
| 3,703,173 | 11/1972 | Dixon ..................................... 128/194 |
| 4,153,689 | 5/1979 | Hirai et al. ............................. 424/178 |
| 4,309,404 | 1/1982 | DeNeale et al. ......................... 424/21 |
| 4,309,406 | 1/1982 | Guley et al. ............................. 424/21 |
| 4,362,719 | 12/1982 | Cavazza et al. ......................... 424/178 |
| 4,529,589 | 7/1985 | Davydov et al. ........................ 424/81 |
| 4,556,552 | 12/1985 | Porter et al. ............................ 424/32 |
| 4,579,730 | 4/1986 | Kidron et al. ............................ 424/19 |
| 4,608,364 | 8/1986 | Grau et al. .................................. 514/4 |
| 4,613,500 | 9/1986 | Suzuki et al. ............................ 429/85 |
| 4,624,251 | 11/1986 | Miller ................................. 128/200.14 |
| 4,635,627 | 1/1987 | Gam ................................... 128/200.14 |
| 4,704,295 | 11/1987 | Porter et al. ............................... 427/3 |
| 4,789,660 | 12/1988 | Enever et al. ............................... 514/4 |
| 4,910,021 | 3/1990 | Davis et al. ............................. 424/456 |
| 4,963,526 | 10/1990 | Ecanow ....................................... 514/3 |
| 4,985,242 | 1/1991 | Sekine et al. ........................... 424/85.4 |
| 4,992,417 | 2/1991 | Katsoyannis et al. ....................... 514/3 |
| 5,011,678 | 4/1991 | Wang et al. ................................ 424/45 |
| 5,053,389 | 10/1991 | Balschmidt et al. ......................... 514/4 |
| 5,112,804 | 5/1992 | Kowarski .................................... 514/3 |
| 5,321,009 | 6/1994 | Baeder et al. ............................... 514/4 |
| 5,518,998 | 5/1996 | Bäckström et al. ......................... 514/3 |

FOREIGN PATENT DOCUMENTS

| 0 200 383 | 7/1986 | European Pat. Off. . |
| 0 272 097 | 12/1987 | European Pat. Off. . |
| 1527605 | 8/1975 | United Kingdom . |
| 85/05029 | 5/1985 | WIPO . |
| 8505029 | 11/1985 | WIPO . |
| 88/02139 | 12/1988 | WIPO . |
| 88/10120 | 12/1988 | WIPO . |
| 91/08760 | 6/1991 | WIPO . |
| 95/00127 | 1/1995 | WIPO . |

OTHER PUBLICATIONS

Eisenbarth, G.S., New Engl. J. Med. 314:1360 (1986).
Prochazka et al. Science 237:286 (1987).
Bendelac et al. J. Exp. Med. 166:823 (1987).
Nagler–Anderson et al., Proc. Nat. Acad. Sci. USA 83:7443 (1986).
Merrifield, R.B., Fed. Proc. Am. Soc. Exp. Biol. 21:412 91962).
Mitchell et al. J. Am. Chem. Soc. 98:7357 (1976).
Tam et al. J. Am. Chem. Soc. 105:6442 (1983).
Newman, S.P., *Aerosols and the Lung*, Clarke, S.W. and Davis, D. eds. pp. 197–224, Butterworths, London, no year given.
Foster, D.W., *Harrison's Principles of Internal Medicine*, Ch. 114, pp. 661–78, 10th Ed., McGraw–Hill, New York, no year given.
Nakhooda et al. Diabetologia 14:199 (1978).
Dayhoff, M.O., *Atlas of Protein Sequence and Structure*, 5:209 (1972).
Gorman, C., Time Magazine, Jun. 10, 1991, p. 54.
Dunlop, M., Toronto Star, May 4, 1991, p. G2.
Rennie, J., Scientific American, 263(6):106, no year given.
Associated Press (Washington), May 25, 1990.
Recer, P., Associated Press (Washington), May 24, 1990.
Cooke, R., Newsday, Dec. 12, 1989, p. 1.
Maugh, T.H., Los Angeles Times, Oct. 12, 1989, p. A3, col. 1.
Biotechnology Newswatch 9(9):5 (1989).
Knox, R.A., The Boston Globe, Feb. 9, 1990, p. 5.
Dean et al. Diabetolgia 29:339 (1986).
Zhang et al. Proc. Nat. Acad. Sci. USA 88:10252 (1991).
Braley–Mullen, H. et al., *Cell. Immunol.* 51:408–413 (1980).
Holt, P.G. et al., *Immunology* 60:97–102 (1987).
Keller, R.J., *J. Autoimmunity* 3:321–327 (1990).
Kono, et al., *J. Exp. Med.* 168:213–227 (1988).
Marx, *Science,* 252:27–28 (1991).
Ziegler, A.G., et al., *Diabetes Care* 13:762–775 (1990).

*Primary Examiner*—Cecilia J. Tsang
*Assistant Examiner*—C. Delacroix-Muirheid
*Attorney, Agent, or Firm*—Darby & Darby

[57] ABSTRACT

Disclosed herein are methods for treating or preventing a disease in mammals having the characteristics of Type 1 diabetes comprising administering insulin or disease suppressive fragments of insulin or analogs thereof in oral or aerosol dosage forms to said mammals. Also disclosed herein are pharmaceutical formulation or dosage forms for use in the methods.

32 Claims, 3 Drawing Sheets

METHOD OF TREATING OR PREVENTING TYPE 1 DIABETES BY ORAL ADMINISTRATION OF INSULIN

This is a continuation, of application Ser. No. 08/235,121, filed Apr. 28, 1994 (now abandoned); which is a continuation of Ser. No. 08/070,020 filed May 28, 1993 (now abandoned), which is a continuation of Ser. No. 07/896,484 filed Jun. 2, 1992 (now abandoned) and which is in turn a continuation of Ser. No. 07/595,468 filed Oct. 10, 1990 (now abandoned).

FIELD OF THE INVENTION

This invention relates to methods and compositions for treating or preventing Type 1 diabetes mellitus. The methods of the invention do not require parenteral administration of therapeutic agents. More particulary, but not by way of limitation, the present invention is directed to agents and methods for treating or preventing autoimmune diseases having the characteristics of Type 1 diabetes mellitus.

BACKGROUND OF THE INVENTION

Diabetes mellitus is characterized in two broad groups based on clinical manifestations, namely, the non-insulin-dependent or maturity onset form, also known as Type 2; and the insulin-dependent or juvenile onset form, also known as Type 1. Clinically, the majority of Type 2, maturity onset diabetics are obese, with manifestations of clinical symptoms of the disease usually appearing at an age over 40. In contrast, Type 1, juvenile onset patients are not over-weight relative to their age and height, with rapid onset of the disease at an early age, often before 30, although Type 1 diabetes can occur at any age.

Diabetes mellitus is a metabolic disorder in humans with a prevalence of approximately one percent in the general population, with one-fourth of these being the Type 1, insulin-dependant category (Foster, D. W., *Harrison's Principles of Internal Medicine*, Chap. 114, pp. 661–678, 10th Ed., McGraw-Hill, N.Y.). The disease manifests itself as a series of hormone-induced metabolic abnormalities which eventually lead to serious, long-term and debilitating complications involving several organ systems including the eyes, kidneys, nerves, and blood vessels. Pathologically, the disease is characterized by lesions of the basement membranes, demonstrable under electron microscopy.

Type 1 diabetics characteristically show very low or immeasurable plasma insulin with elevated glucagon. Regardless of what the exact etiology is, most Type 1 patients have circulating antibodies directed against their own pancreatic cells including antibodies to insulin, to islet of Langerhans cell cytoplasm and to the enzyme glutamic acid decarboxylase. An immune response specifically directed against beta cells (insulin producing cells) leads to Type 1 diabetes. This specificity is supported by the above clinical picture, since beta cells secrete insulin while alpha cells secrete glucagon.

Current therapeutic regimens for Type 1 diabetes include modifications to the diet in order to minimize hyperglycemia resulting from the lack of natural insulin, which in turn, is the result of damaged beta cells. Diet is also modified with regard to insulin administration to counter the hypoglycemic effects of the hormone. Whatever the form of treatment, parenteral administration of insulin is required for all Type 1 diabetics, hence the term "insulin-dependent" diabetes.

Conventional insulin therapy is limited to the parenteral (i.e. subcutaneous) administration of insulin. Oral administration of insulin has not been possible because the insulin molecule cannot pass through the digestive tract in a sufficiently intact form to provide its therapeutic benefit. There has been an ongoing search by those skilled in the art for an alternative method to eliminate or reduce the need for insulin because of the numerous problems associated with subcutaneous administration of the drug. Among the methods that have been investigated are implantable insulin pumps and pancreatic islet cell transplantation.

Because Type 1 diabetes usually manifests itself in adolescents and because the subcutaneous delivery of insulin requires strict, self-regimentation, compliance is often a serious problem. In addition, the act of the parenteral administration itself can be very traumatic to juveniles. For the clinician, it is difficult to precisely regulate the amounts of insulin needed at any given time of the patient's day. Furthermore, it is all but impossible to regulate blood glucose levels in diabetic patients with parenteral insulin to the extent to which blood glucose is regulated in normal individuals.

Thus, in the early stages of treatment of Type 1 diabetes, patients often become either hyperglycemia or hypoglycemic because the exact timing of the insulin injections and levels of insulin needed are not known. As treatment progresses the clinician and, more importantly, the patient adjusts to the daily routine, but there is always the risk of ketoacidosis or hypoglycemia.

In addition, some patients produce antibodies to the injected insulin even though most patients are now treated with human insulin produced by recombinant technology. This can lead to the need for higher doses of insulin. To date, there has been no successful oral dosage form containing insulin.

The art has long sought a method for preventing and/or treating Type 1 diabetes which does not involve parenteral administration of insulin. Various attempts at alternate delivery methods for insulin have failed or have not progressed to a practical level. For example, oral insulin, transcutaneous insulin delivery, and nasal insulin have not become clinically utilized. Oral insulin does not affect blood glucose levels. Because it has been necessary to inject lipids into mammals receiving nasal insulin in order to get the insulin across the nasal mucosa, this route of insulin administration has been limited.

Oral dosage forms for treatment of Type 2 diabetes are available, (e.g. oral sulfonylureas). These orally administered agents do not comprise insulin but rather stimulate the pancreas to produce insulin, and are only effective for treatment of certain forms of Type 2 diabetes. As for Type 1 diabetes, oral agents such as sulfonylureas are ineffective due to markedly diminished or damaged beta-cell mass (Foster, D. W., *Harrison's Principles of Internal Medicine*, Chap. 114, p. 668, 10th Ed., McGraw-Hill, N.Y.).

Type 1 diabetes is considered to be a disease of autoimmune etiology (Eisenbarth, G. S., *New Engl. J. Med.* 314: 1360–1368, 1986). Various animal models are available for the study of Type 1 diabetes as an autoimmune disorder. These include the BB mouse (Nakbookda, A. F., et al., *Diabetologic* 14: 199–207, 1978) and the NOD (non-obese diabetic) mouse in which diabetes develops spontaneously (Prochazka et al. *Science* 237:286, 1987). Islet-cell specific, CD4 and CD8 T-lymphocytes have been implicated as causative agents for damage to beta cells, demonstrated by decreased incidence of Type 1 diabetes in NOD mice (*J. Exp. Med.* 166:823, 1987).

Other therapies are being developed for the treatment of autoimmune diseases in general.

Weiner et al., U.S. patent application Ser. No. 460,852 filed Feb. 21, 1990, (the national stage of PCT Application No. PCT/US88/02139, filed Jun. 24, 1988), which is a continuation-in-part application of U.S. patent application Ser. No. 065,734 filed Jun. 24, 1987, discloses the treatment of autoimmune diseases by oral administration of autoantigens.

Weiner et al., U.S. patent application Ser. No. 454,486 filed Dec. 20, 1989, discloses the aerosol administration of autoantigens, disease-suppressive fragments of said autoantigens and analogs thereof as an effective method for treating T-cell mediated autoimmune diseases.

Weiner et al., U.S. patent application Ser. No. 487,732, filed Mar. 2, 1990, discloses synergists (enhancers) for use with oral administration of autoantigens, disease suppressive fragments and analogs thereof as effective treatments for T-cell mediated autoimmune diseases.

Weiner et al., U.S. patent application Ser. No. 551,632 filed Jul. 10, 1990, as a Rule 62 continuation-in-part application of U.S. patent application Ser. No. 379,778, filed Jul. 14, 1989 (now abandoned), discloses methods of preventing or treating uveoretinitis in mammals by oral administration of purified S antigen.

Nagler-Anderson, et al., (Proc. Natl. Acad. Sci (USA) 83: 7443–7446, 1986), describe the oral administration of collagen to suppress collagen-induced arthritis in a mouse model.

However, none of the above-mentioned for treatments for autoimmune diseases can be used treating Type 1 diabetes because the antigens involved in eliciting and maintaining the Type 1 disease have not been identified.

It is, therefore, an object of the present invention to provide agents and methods for treating and preventing autoimmune diseases in mammals having the characteristics of Type 1 diabetes. Prevention of Type 1 diabetes preferably involves treatment prior to hyperglycemia.

Another object of the present invention is to provide compositions and pharmaceutical formulations useful for treating mammals suffering from autoimmune diseases having the characteristics of Type 1 diabetes.

A still further object of the invention is to provide compositions and pharmaceutical formulations useful for oral administration to mammals for the purpose of preventing or attenuating the manifestations (i.e. clinical symptoms) of autoimmune diseases having the characteristics of Type 1 diabetes. Prevention of Type 1 diabetes includes treatment prior to hyperglycemia.

These and other objects of the present invention will be apparent to those of ordinary skill in the art in light of the following.

SUMMARY OF THE INVENTION

It has unexpectedly been discovered that oral administration of insulin is an effective treatment for eliminating or reducing the need for insulin in Type 1 diabetics. Oral insulin can prevent or ameliorate beta cell destruction and thereby decrease or eliminate traditional parenteral insulin therapy.

Orally administerable pharmaceutical formulations containing insulin are prepared and administered to mammals who have manifested symptoms of Type 1 diabetes and/or diagnosed as having Type 1 diabetes. Additionally, subjects who are at risk for developing Type 1 diabetes ( i.e. have demonstrated a predisposition to developing Type 1 diabetes through suitable means, such as genetic studies and analysis) are treated with similar oral preparations of insulin.

Pharmaceutical formulations for oral or enteral administration to treat Type 1 diabetes are prepared from commercially available insulin and a pharmaceutically acceptable carrier suitable for oral ingestion. The quantity of insulin in each dose may be between 1 mg and 1000 mg. However the total dose required for treatment varies according to the individual. Generally, the total quantity of insulin required in practicing the present invention is a much larger dose than is the dosage that is administered parenterally to protect an individual afflicted with Type 1 diabetes against ketoacidosis.

Additionally, an aerosol delivery system can be made with similar dosages of insulin as above with a pharmaceutically suitable carrier or diluent. These and other improvements will be described in the following descriptions, drawings and the appended claims.

DETAILED DESCRIPTION OF THE INVENTION

Figure 1:
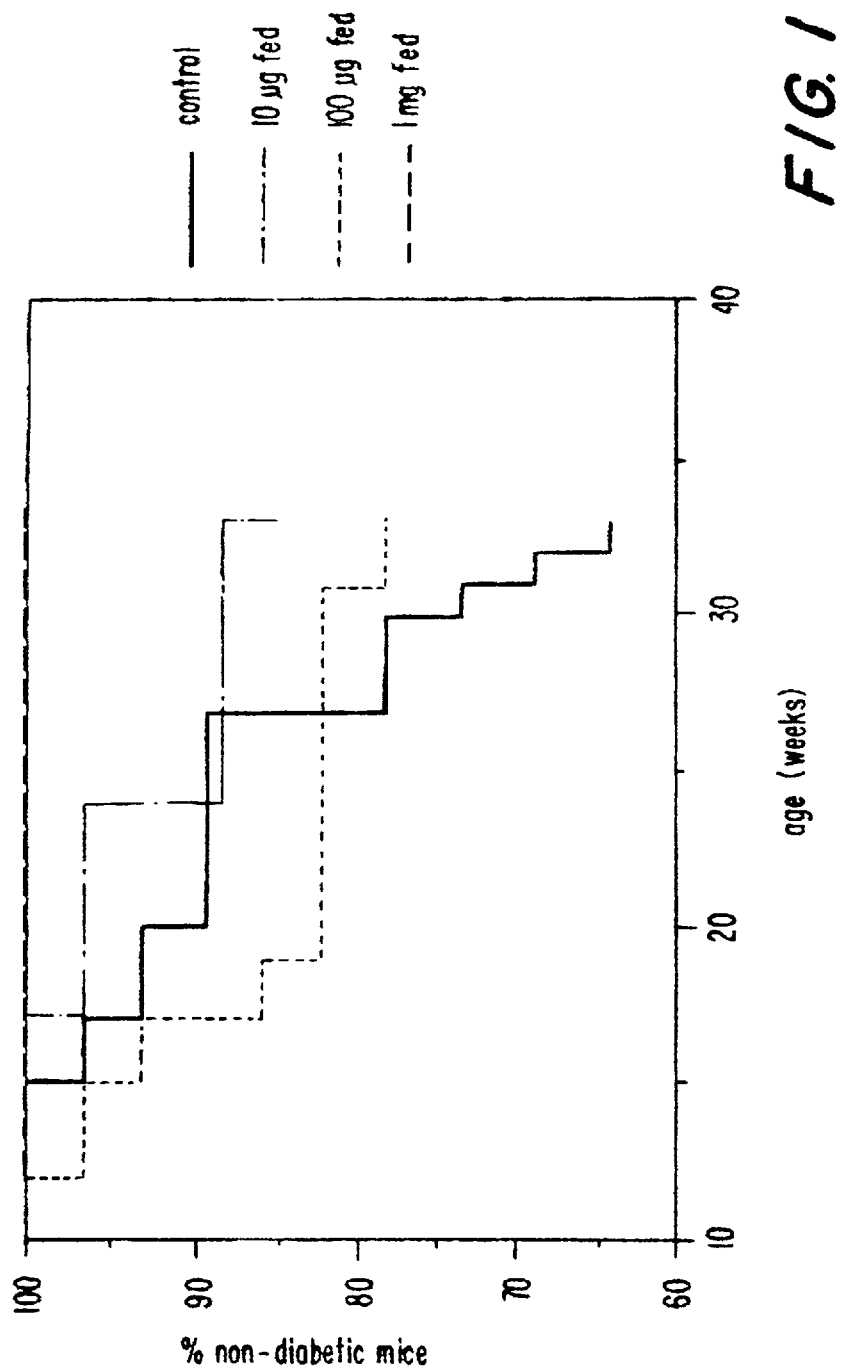
FIG. 1 is a graph showing the effects of orally administered porcine insulin on diabetes in NOD mice.

All patent applications, patents and literature references referred to herein are hereby incorporated by reference in their entirety.

The present invention addresses the need for an alternate to existing methods for the treatment of Type 1 diabetes from an autoimmune model and in particular at treatment for the prevention of diabetes. Because Type 1 patients are predominantly adolescents, it is believed that long term insulin therapy will no longer be required due to preservation of undamaged beta cell function if treatment is initiated at the onset of the disorder using the compositions and methods of the present invention. In addition, if the methods of the present invention are initiated at a time when some beta cell function still exists, parenteral insulin therapy can be reduced. Thus, the present invention provides means whereby long term insulin therapy would be reduced or no longer be required.

It has now been unexpectedly discovered that oral and/or aerosol administration of insulin (or disease-suppressive fragments of insulin or analogs thereof) is effective for the treatment and prevention of Type 1 diabetes. This is a radical departure from traditional (parenteral) insulin therapy in that insulin is adminstered in order to damp down or shut off the hosts autoimmune response and not for its endocrinologic (metabolic) effect. Oral administration of insulin has not proved to be effective in treating any form of diabetes because proteolytic enzymes present in the stomach and digestive system degrade the polypeptide before it can reach the bloodstream. In addition, intranasal administration of insulin has also not previously been shown to be effective in treating any form of diabetes.

Without wishing to be bound by theory of operation it is believed that the oral or aerosol administration of insulin pursuant to the present invention affects the immunological pathogenesis of Type 1 diabetes through the elicitation of suppressor T-cells.

In the following discussions the following terms shall have the meaning ascribed to them below.

"Treatment" shall mean the treatment of active disease in patients with some level of undamaged, insulin-producing beta cells as well as prophylactic administration for use in patients having a high risk for developing the disease.

"Oral administration" shall mean both oral administration and enteral administration (direct incubation into the stomach).

"Individuals at risk" for Type 1 diabetes shall mean a) individuals having a blood relative with Type 1 diabetes; b) autoantibody-positive individuals without overt Type 1 diabetes. These auto antibodies include cytoplasmic islet cell autoantibodies, insulin antibodies and glutamic acid decarboxylase autoantibodies; c) individuals with Histocompatibility (HLA) type DR3 or DR4DQW8; d) individuals with glucose abnormalities such as a loss of first phase insulin secretion on glucose tolerance tests.

"Mammal" shall mean any organism having an immune system and therefore susceptible to Type 1 diabetes.

"Active disease", shall mean autoimmune destruction of islet beta cells.

"Aerosol" refers to finely divided solid or liquid particles that may be created using a pressurized system such as a nebulizer. The liquid or solid source material contains insulin and/or disease suppressive fragments of insulin and analogs thereof as defined herein.

"Disease suppressive fragments" of insulin includes any peptide or polypeptide containing partial amino acid sequences or moieties of insulin and possessing the ability to treat or prevent a disease having the characteristics of Type 1 diabetes. Such fragments need not possess the autoantigenic or endocrinolocic (metabolic) properties of the entire insulin molecule.

"Analogs" of insulin or disease suppressive fragments thereof refers to compounds that are structurally related to insulin or disease suppressive fragments thereof which possess the same biologic activity, i.e., the ability to suppress or prevent disease symptoms of Type 1 diabetes, upon oral or aerosol administration. By way of non-limiting example, the term includes peptides having amino acid sequences which differ from the amino acid sequence of insulin or disease suppressive fragments thereof by one or more amino acid residues while still retaining the disease suppressive activity of insulin or its ability to prevent or alleviate the symptoms of Type 1 diabetes. These analogs do not necessarily need to possess the endocrinologic effects of insulin.

In accordance with the present invention, experiments were performed in which NOD (non-obese diabetic) mice, which develop diabetes spontaneously between 11 and 52 weeks of age, had a lower incidence of diabetes at all doses of orally administered insulin in a dose-dependent manner. In all of the animals which received the highest dose of oral insulin (1 mg), 100% of the treated animals failed to develop diabetes.

Although it is fairly easy to control the symptoms of Type 1 diabetes with parenteral insulin, it is difficult to normalize a patient's blood sugar throughout 24 hours utilizing traditional insulin therapy given as 1 or 2 injections a day. Thus, the present invention provides a method for treating or preventing a disease having the characteristics of Type 1 diabetes in a mammal comprising administering to a mammal, suffering from or at risk for Type 1 diabetes, an effective amount of an oral insulin dosage form to treat or prevent the symptoms of diabetes.

It should be noted that the methods of the present invention will not eliminate the need for parenteral insulin therapy in patients with damaged beta cells who do not produce enough insulin to regulate their blood sugar. However, using the methods and compositions of the present invention, newly diagnosed Type 1 diabetic patients or those at risk for the disease (as defined above), who have substantially intact (undamaged) beta cells, will not go on to develop Type 1 diabetes and parenteral insulin administration may be eliminated. In addition, it is believed that the methods and compositions of the present invention will reduce the amount of insulin needed by those individuals having some beta cell function (who are able to produce some level of insulin) by halting progression of the disease.

Insulin for use in the present invention can be obtained from numerous commercial sources such as Novo Laboratories (Danbury, Conn.), Nordisk-USA (Rockville, Md.) and Eli Lilly and Co. (Indianapolis, Ind). Porcine-derived insulin, human semi-synthetic insulin (Nordisk-U.S.A) and cloned recombinant insulin (Eli Lilly) can be used when practicing the method of the present invention.

Disease suppressive fragments and analogs of insulin for use in the present invention can be synthesized using well known solid phase synthesis techniques (Merrifield, R. B. *Fed. Proc. Am. Soc. Ex. Biol.* 21: 412, 1962 and *J. Am. Chem. Soc.* 85: 2149, 1963; Mitchel, A. R. et al., *J. Am. Chem. Soc.* 98: 7357, 1976; Tam, J. et al., *J. Am. Chem. Soc.* 105: 6442, 1983). Analogs can be constructed by identifying an equivalent amino acid sequence and using the peptide synthesis techniques disclosed above.

Analogs can be provided using the known amino acid sequence of insulin as disclosed in *Atlas of Protein Sequence and Structure, Natl. Biochem. Res. Foundation*, vol. 5, pgs. 209–211.

Disease-suppressive analogs and fragments can also be obtained using recombinant DNA techniques well-known in the art.

Disease suppressive fragments of insulin and analogs thereof can be identified using routine experimentation using suitable in vivo systems such as those of Examples 1–5 below.

Pursuant to the present invention, insulin or disease suppressive fragments or analogs thereof are introduced into a mammal suffering from or at risk for a disease having the characteristics of Type 1 diabetes, orally or enterally, in an amount of between about 2 mg per kg body weight of said mammal and about 10 mg per kg body weight of said mammal per day, and may be administered in a single dose form or multiple dose forms. Preferably, the insulin is administered in an amount between about 2.5 mg and about 5.0 mg per kg body weight of said mammal per day. The exact amount to be administered will vary depending on the severity and stage of a patient's disease and the physical condition of the patient.

The present invention also is directed to oral dosage forms and pharmaceutical formulations for administration to mammals suffering from or at risk for diseases having the characteristics of Type 1 diabetes. It will be understood that any statistically significant attenuation in the disease symptoms of Type 1 diabetes pursuant to the treatment of the present invention is within the scope of the invention.

Each oral formulation according to the present invention may additionally comprise inert constituents including pharmaceutically acceptable carriers, diluents, fillers, solubilizing or emulsifying agents and salts as is well-known in the art. For example, tablets may be formulated in accordance with conventional procedures employing solid carriers well-known in the art. Capsules employed in the present invention may be made from any pharmaceutically acceptable material such as gelatin or cellulose derivatives. Sustained release oral delivery systems and/or enteric coatings for orally administered dosage forms are also contemplated such as those described in U.S. Pat. No. 4,704,295 issued Nov. 3, 1987, U.S. Pat. No. 4,556,552 issued Dec. 3, 1985, U.S. Pat. No. 4,309,404 issued Jan. 5, 1982 and U.S. Pat. No. 4,309,406 issued Jan. 5, 1982.

Examples of solid carriers include bentonite, silica and other commonly used carriers. Further non-limiting examples of carriers and diluents which may be used in the formulations of the present invention include saline and any physiologically buffered saline solution such as phosphate buffered saline (PBS) and water.

It will be appreciated that the unit content of active ingredient or ingredients contained in an individual dose of each dosage form need not in itself constitute an effective amount since the necessary effective amount can be reached by administration of a plurality of dosage units.

The preferred route of administration of the dosage forms of the present invention is orally or enterally. Preferred oral or enteral pharmaceutical formulations or dosage forms may comprise for example, between about 1 mg and about 1000 mg of insulin.

In an alternative preferred embodiment of the present invention the pharmaceutical formulations or dosage forms of the present invention can also be administered to mammals suffering from diseases having the characteristics of Type 1 diabetes in aerosol form. It is expected that lower amounts of insulin, disease suppressive fragments or analogs thereof will be required using aerosol administration for treating or preventing Type 1 diabetes as has been found when treating experimental allergic encephalomyelitis (EAE) with myelin basic protein (MBP) and adjuvant arthritis with collagen as disclosed in co-pending U.S. patent application Ser. No. 454,486 filed Dec. 20, 1989. The amounts of insulin or disease suppressive fragments or analogs thereof which may be administered in an aerosol dosage form would be between about 0.1 mg and 10 mg per kg body weight of a mammal per day and may be administered in single dosage form or multiple dosage forms. The exact amount to be administered will vary depending on the state and severity of a patient's disease and the physical condition of the patient.

The aerosol pharmaceutical formulations of the present invention may include, as optional ingredients, pharmaceutically acceptable carriers, diluents, solubilizing or emulsifying agents, and salts of the type that are well-known in the art. Examples of such substances include normal saline solutions, such as physiologically buffered saline solutions, and water.

The route of administration of insulin or disease suppressive fragments or analogs thereof according to this alternate embodiment of the present invention is in an aerosol or inhaled form. The insulin and related compounds of the present invention can be administered as a dry powder or in an aqueous solution. Preferred aerosol pharmaceutical formulations may comprise for example, a physiologically-acceptable buffered saline solution containing between about 1 mg and about 1000 mg of insulin, disease suppressive fragments or analogs thereof.

Dry aerosol in the form of finely divided solid particles of insulin, disease suppressive fragments or analogs thereof that are not dissolved or suspended in a liquid are also useful in the practice of the present invention. The insulin may be in the form of dusting powders and comprise finely divided particles having an average particle size of between about 1 and 5 microns, preferably between 2 and 3 microns. Finely divided particles may be prepared by pulverization and screen filtration using techniques well known in the art. The particles may be administered by inhaling a predetermined quantity of the finely divided material, which can be in the form of a powder.

Specific non-limiting examples of the carriers and/or diluents that are useful in the aerosol pharmaceutical formulations of the present invention include water and physiologically-acceptable buffered saline solutions such as phosphate buffered saline solutions pH 7.0–8.0.

The pharmaceutical formulations of the present invention may be administered in the form of an aerosol spray using for example, a nebulizer such as those described in U.S. Pat. Nos. 4,624,251 issued Nov. 25, 1986; 3,703,173 issued Nov. 21, 1972; 3,561,444 issued Feb. 9, 1971 and 4,635,627 issued Jan. 13, 1971. The aerosol material is inhaled by the subject to be treated.

Other systems of aerosol delivery, such as the pressurized metered does inhaler (MDI) and the dry powder inhaler as disclosed in Newman, S. P. in *Aerosols and the Lung*, Clarke, S. W. and Davia, D. eds. pp. 197–224, Butterworths, London, England, 1984, can be used when practicing the present invention.

Aerosol delivery system of the type. disclosed herein are available from numerous commercial sources including Fisons Corporation (Bedford, Mass.) Schering Corp. (Kenilworth, N.J.) and American Pharmoseal Co., (Valencia, Calif.).

It is expected that the methods of the present invention are particularly well-suited for use in pediatric or adolescent patients developing Type 1 diabetes or the first year of onset of hyperglycemia in whom the secondary effects of the disease (such as vascular damage, kidney damage and diabetic retinopathy) have not been totally manifested. These are also the patients in whom the traumatic effects of daily insulin injections are usually most severely felt.

As shown in the examples presented below, oral administration of insulin to NOD mice reduced the numbers of these mice which subsequently went on to develop diabetes at all dosages tested. in addition, at the highest dose used (1 mg), none of the mice went on to develop diabetes. In addition, as shown in Example 2, the effects of oral insulin were not due to a reduction in the serum glucose concentrations in these animals and was thus not a metabolic effect. In addition, as shown in Example 3 below, feeding NOD mice pancreatic extract also led to a diminution in the number of animals which developed diabetes although to a lesser extent than those that received oral insulin.

Preliminary experiments have shown that NOD mice fed 1 mg of insulin had fewer inflammatory immune system cells surrounding the pancreas (a condition known as insulitis) than PBS-fed NOD mice (data not shown). Therefore, oral administration of insulin to NOD mice appeared to be affecting the infiltration of immune system cells into the pancreas and thus halting disease progression by preserving beta cell function.

The present invention is described further below in working examples which are intended to illustrate the present invention without limiting its scope.

EXAMPLE 1

EFFECT OF FEEDING PORCINE-INSULIN ON SPONTANEOUS DIABETES IN NOD MICE

NOD (non-obese diabetic mice) were obtained from Taconic Laboratories (Germantown, Mass.) at 4 weeks of age. There were a total of 30 animals in each of the groups mentioned below at the beginning of the experiment. At 4½ weeks of age, animals were orally administered Porcine insulin (Novo Laboratories, Danbury, Conn.). Each animal received two treatments orally twice a week until 9 weeks of age. The mice were fed either saline (control) or 10 micrograms, 100 micrograms, or 1 milligram of Porcine insulin. The animals were fed (gavaged) with an 18 gauge ball-point needle (Popper and Sons, Inc., New Hyde Park, N.Y.). Beginning at 10 weeks the animals were then fed once a week for a total of 33 weeks. Beginning at 12 weeks the urine was tested weekly for the presence of glucose using Glucosuria test tape (Eli Lilly, Indianapolis, Ind.). If an animal tested 3+ or higher on the glucose urine test, a serum sample was taken and blood glucose measured using a glucose analyzer (Beckman). If the blood glucose was 220 or higher, the animals were classified as diabetic and then sacrificed.

As shown in FIG. 1, no diabetes developed in any of the animals fed 1 mg insulin whereas diabetes developed in the control group and in the 10 microgram and 100 microgram groups in a dose response fashion. The p value comparing the 1 mg fed to the control is $p<0.008$ whereas in the 100 microgram fed, $p<0.09$.

The normal blood insulin level in an animal is between 120 to 170 mg/decaliter or mg/dl. The blood sugars in the animals that were fed PBS that developed diabetes were: 575, 485, 459, 500, 375, 400, 362, 395, 480 mg/dl. The blood sugar in the animals that were fed 10 micrograms of insulin which developed diabetes were: 330, 420, 315, 459, 520, 487 mg/dl. Blood sugars in animals fed 100 micrograms of insulin that became diabetic were: 290, 600, 450, 500 mg/dl. Animals that were fed 1 mg of insulin were also tested in terms of blood sugar. None of the animals developed diabetes as measured by urine testing but the blood sugar was tested as a confirmation. Blood sugar on 10 representative animals from the group fed 1 mg insulin were: 174, 128, 125, 125, 145, 123, 136, 155, 115, 130 mg/dl.

EXAMPLE 2

GLUCOSE POST ORAL INSULIN IN FASTING 7 WEEK NOD MICE

In order to determine whether any endocrinologic (i.e. direct lowering of blood sugar) effects occurred following the feeding of insulin, 7 week old NOD mice (5 mice per group) were fed 1 mg of porcine insulin or 1 mg of myelin basic protein (obtained from Pel Freez, Rogers, AR) as a control protein. Blood glucose was then measured over the next 24 hour period. As a positive control, a separate group of animals were injected subcutaneously with 20 micrograms of Porcine insulin. All animals were kept in the fasting state.

Figure 2:
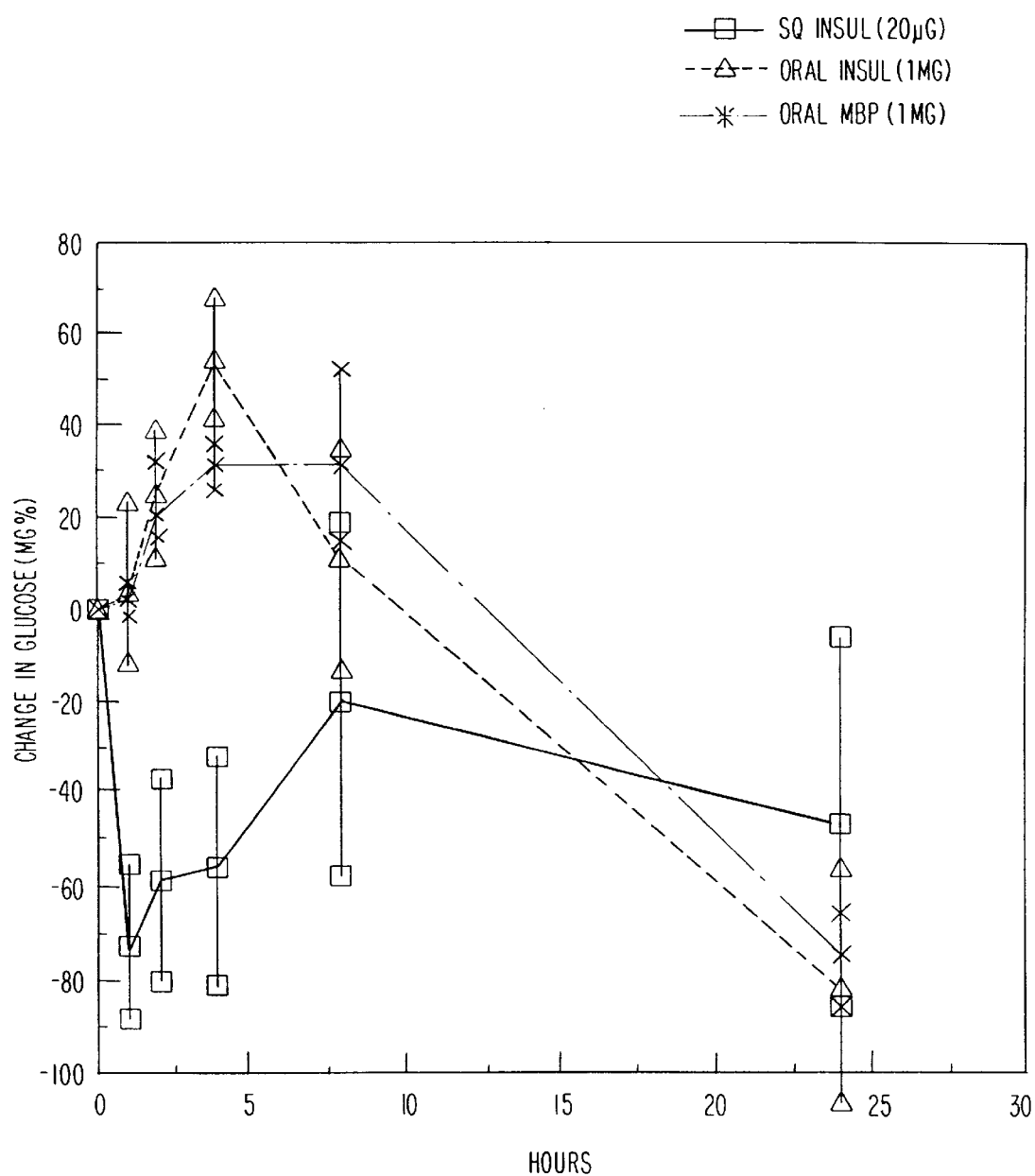
FIG. 2 is a graph showing the effects of oral porcine insulin on serum glucose concentrations post-administration of oral insulin in NOD mice.

As shown in FIG. 2, animals given subcutaneous insulin had an immediate drop in the glucose level with a decrease of approximately 80 mg % that persisted over a 4 hour period and then slowly returned to normal. Animals which received oral insulin or oral myelin basic protein had no drop in the blood glucose; in fact there was an increase in blood glucose most probably related to the protein load. Over the next 24 hours there was a gradual decrease in blood glucose in all groups of animals since the animals were in a fasting state. This was seen both in animals fed insulin and animals fed myelin basic protein.

These results demonstrate that there were no endocrinologic (metabolic) effects from feeding oral insulin. Given the published data in terms of generating immunologic tolerance and immunologic effects following the oral administration of proteins these results strongly suggest that oral administration of insulin affects the immunologic pathogenesis of diabetes in the NOD mice.

EXAMPLE 3

EFFECT OF ORAL ADMINISTRATION OF PANCREATIC EXTRACT GIVEN AT WEEKLY INTERVALS

Figure 3:
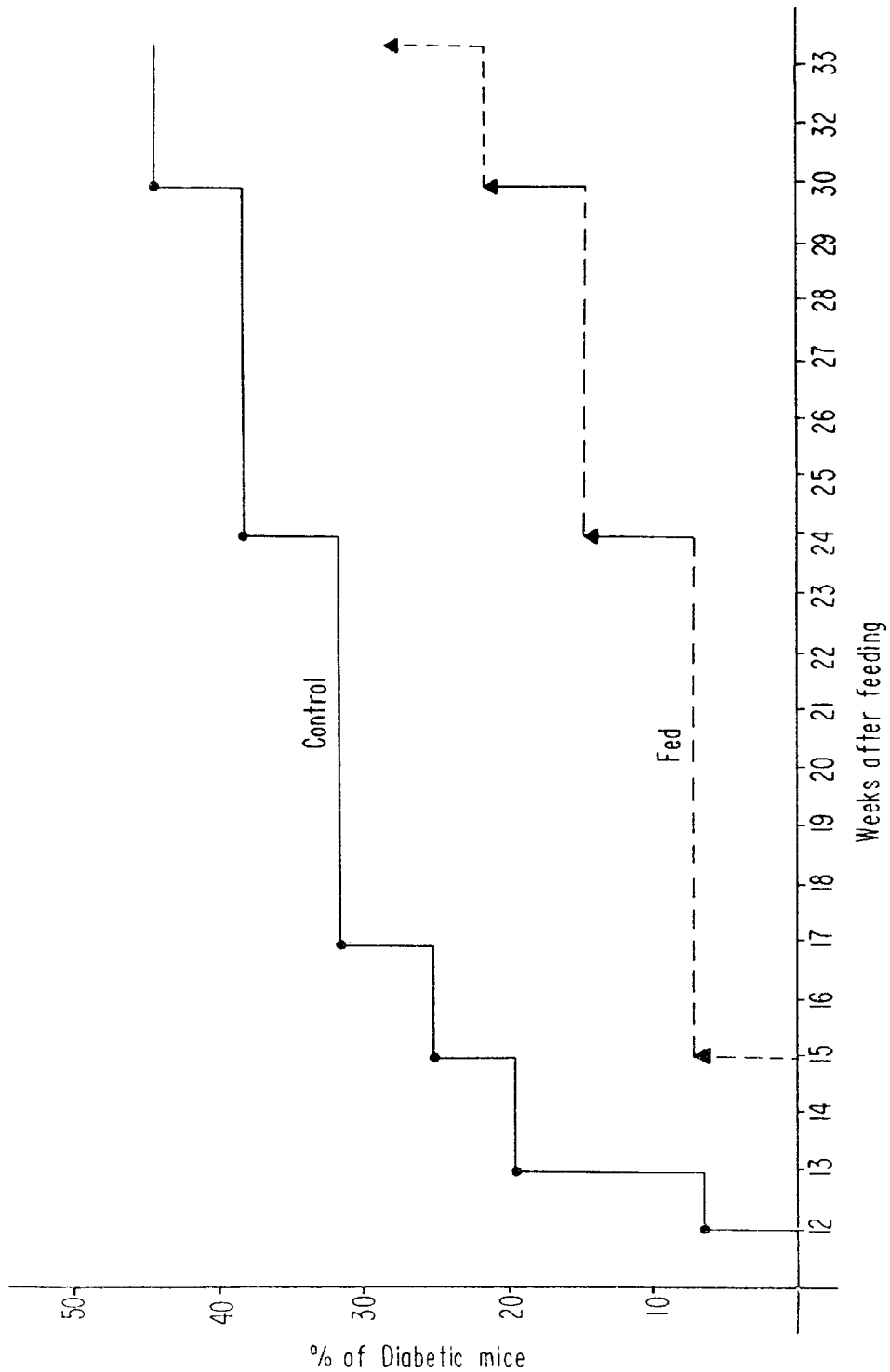
FIG. 3 is a graph showing the effect of oral administration of pancreatic extracts given at weekly intervals on the development of diabetes in NOD mice.

An identical experiment to Example 1 was performed in which NOD mice (14–17 per group) were fed one homogenized pancreas derived from Lewis rats in 0.5 mls PBS. As shown in FIG. 3, there was a decrease in the development of diabetes in extract-fed animals as compared to controls. Nonetheless, the effect is not as dramatic and complete as that seen in the animals fed insulin. These results show some effect of feeding pancreatic tissue and highlight the potency of the insulin experiments described above.

EXAMPLE 4

EFFECT OF AEROSOL ADMINISTRATION OF INSULin ON DIABETES IN NOD MICE

Insulin (0 to 1 mg as in Examples 1 and 2) will be administered to NOD mice as described above in Examples 1 and 2 except in aerosol form by nebulizer.

It is expected that aerosolized insulin will be effective in preventing the manifestation of symptoms (i.e. hyperglycemia) of Type 1 diabetes in the treated mice.

EXAMPLE 5

TREATMENT OF INITIAL STAGES OF DIABETES IN NOD MICE

Insulin (0 to 1 mg as in Examples 1 and 2) will be administered to NOD mice which are suffering from hyperglycemia in an oral and aerosol form. The treatments will begin by weeks 12–20 of age, by which the serum glucose levels are at hyperglycemic concentrations in a certain percentage of animals prior to onset of diabetes.

It is expected that both oral and aerosol administration of insulin will lead to reduction in serum glucose concentrations to near normal levels and preservation of beta cell function.

What is claimed is:

1. A method for suppressing an autoimmune response against pancreatic beta cells in a mammal in need of suppression of said autoimmune response, comprising nasally or by mouth administering to said mammal an effective amount of a composition comprising insulin or a fragment of insulin having the property of suppressing said autoimmune response, wherein said composition is effective to suppress said autoimmune response without causing a decrease in the blood sugar level of said mammal within four hours after said administration.

2. The method of claim 1, wherein said mammal suffers from a disease selected from the group consisting of Type 1 diabetes and animal disease states that serve as models for Type 1 diabetes.

3. The method of claim 1, wherein said composition comprises insulin.

4. The method of claim 1, wherein the administration continues in single or multiple doses for at least 12 weeks.

5. A method for treating a mammal suffering from Type 1 diabetes by suppressing an autoimmune response associated with said disease, said mammal maintaining at least partial pancreatic beta cell function, the method comprising nasally or by mouth administering to said mammal a composition containing an effective amount of insulin or a fragment of insulin having the property of suppressing said autoimmune response, wherein said composition is effective to suppress said autoimmune response without causing a decrease in blood sugar level of said mammal within four hours after said administration.

6. The method of claim 5, wherein said administration suppresses autoimmune destruction of pancreatic beta cells.

7. The method claim of claim 5, wherein said composition comprises insulin.

8. The method of claim 5, wherein said administration is via the nasal route.

9. The method of claim 5, wherein the administration continues in single or multiple doses for at least 12 weeks.

10. A method for preventing or suppressing the onset of type 1 diabetes in a mammal in need of prevention or suppression of said onset by suppressing an autoimmune response associated with said diabetes which comprises the steps of:
   nasally or by mouth administering to said mammal an effective amount for preventing or suppressing the onset of Type 1 diabetes of a composition comprising insulin or a fragment of insulin having the property of suppressing said autoimmune response, wherein said composition is effective to prevent to suppress said onset without causing a decrease in the blood sugar level of said mammal within for hours after said administration.

11. The method of claim 10, wherein said administration suppresses autoimmune destruction of pancreatic beta cells.

12. The method of claim 10, wherein said composition comprises insulin.

13. The method of claim 10, wherein the administration continues in single or multiple doses for at least 12 weeks.

14. A method for suppressing an autoimmune response against pancreatic beta cells in a mammal in need of suppression of said autoimmune response comprising nasally or by mouth administering to said mammal an effective amount of a composition comprising an autoimmune response suppressive analog of insulin having at least one antigenic determinant of insulin and having the property of suppressing said autoimmune response, wherein said composition is effective to suppress said autoimmune response without causing a decrease in the blood sugar level of said mammal within four hours after said administration.

15. The method of claim 14 wherein said mammal suffers from a disease selected from the group consisting of Type 1 diabetes and animal disease states that serve as models for Type 1 diabetes.

16. The method of claim 14 wherein said administration is via the nasal route.

17. The method of claim 14, wherein the administration continues in single or multiple doses for at least 12 weeks.

18. A method for treating a mammal suffering from Type 1 diabetes by suppressing an autoimmune response associated with said disease, said mammal maintaining at least partial pancreatic beta cell function, the method comprising nasally or by mouth administering to said mammal a composition comprising an analog of insulin having at least one antigenic determinant of insulin and having the property of suppressing said autoimmune response, wherein said composition is effective to suppress said autoimmune response without causing a decrease in the blood sugar level of said mammal within four hours after said administration.

19. The method of claim 18 wherein said administration suppresses autoimmune destruction of pancreatic beta cells.

20. The method of claim 18 wherein said administration is via the nasal route.

21. The method of claim 18, wherein the administration continues in single or multiple doses for at least 12 weeks.

22. A method for preventing or suppressing the onset of Type 1 diabetes in a mammal in need of prevention or suppression of said onset by suppressing autoimmune response associated with said diabetes which comprises the step of:
   prior to occurrence of hyperglycemia nasally or by mouth administering to said mammal an effective amount for preventing or suppressing the onset of Type 1 diabetes of a composition comprising an analog of insulin having at least one antigenic determinant of insulin and having the property of suppressing said autoimmune response, wherein said composition is effective to prevent or suppress said onset without an accompanying substantial decrease in the blood sugar level of said mammal within four hours after said administration.

23. The method of claim 22 wherein said administration suppresses autoimmune destruction of pancreatic beta cells.

24. The method of claim 22 wherein said administration is via the nasal route.

25. The method of claim 22, wherein the administration continues in single or multiple doses for at least 12 weeks.

26. A method for treating a mammal suffering from Type 1 diabetes by suppressing autoimmune response associated with said disease, said mammal maintaining at least partial pancreatic beta cell function, the method comprising nasally administering to said mammal a composition containing an effective amount of insulin, wherein said composition is effective to suppress said autoimmune response without causing a disease in blood sugar level of said mammal within four hours after said administration, and wherein said administration continues in single or multiple doses for at least 12 weeks.

27. A method for preventing or suppressing the onset of Type 1 diabetes in a mammal in need of prevention or suppression of said onset by suppressing autoimmune response associated with said diabetes which comprises the step of nasally administering to said mammal an effective amount for preventing or suppressing the onset of Type 1 diabetes of a composition comprising insulin, wherein said composition is effective to prevent or suppress said onset without an accompanying substantial decrease in the blood sugar level of said mammal within four hours after said administration, said administration continuing in single or multiple doses for at least 12 weeks.

28. A method for suppressing autoimmune response against pancreatic beta cells in a mammal comprising administering nasally or by mouth to said mammal an amount of a fragment of insulin effective to suppress said autoimmune response, said fragment being incapable of causing an accompanying decrease in the blood sugar level of said mammal.

29. A method for suppressing autoimmune response against pancreatic beta cells in a mammal comprising administering nasally or by mouth to said mammal an amount of an analog of insulin effective to suppress said autoimmune response, said analog being incapable of causing an accompanying decrease in the blood sugar level of said mammal.

30. A method for treating an individual suffering from Type 1 diabetes and maintaining at least partial pancreatic beta cell function, comprising the step of administering nasally or by mouth to said individual a composition containing an amount of a fragment of insulin effective to suppress an autoimmune response associated with said disease, without causing a decrease in blood sugar level of said individual within 4 hours after said administration.

31. A method for treating an individual suffering from Type 1 diabetes and maintaining at least partial pancreatic beta cell function, comprising the step of nasally or by mouth administering to said individual to said individual a composition containing an amount of an analog of insulin effective to suppress an autoimmune response associated with said disease, without causing a decrease in blood sugar level of said individual within 4 hours after said administration.

32. The method of claim 31 wherein said analog comprises insulin.

* * * * *